US010262219B2

(12) United States Patent
Kim et al.

(10) Patent No.: US 10,262,219 B2
(45) Date of Patent: Apr. 16, 2019

(54) APPARATUS AND METHOD TO DETERMINE DROWSINESS OF A DRIVER

(71) Applicant: Hyundai Motor Company, Seoul (KR)

(72) Inventors: Sam Yong Kim, Gyeonggi-do (KR); Byoung Joon Lee, Gyeonggi-do (KR); Seong Sook Ryu, Seoul (KR); Jin Kwon Kim, Gyeonggi-do (KR); Ho Choul Jung, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 271 days.

(21) Appl. No.: 15/289,824

(22) Filed: Oct. 10, 2016

(65) Prior Publication Data
US 2017/0308762 A1 Oct. 26, 2017

(30) Foreign Application Priority Data

Apr. 21, 2016 (KR) .................. 10-2016-0048915

(51) Int. Cl.
G06K 9/00 (2006.01)
A61B 5/00 (2006.01)
A61B 5/16 (2006.01)
A61B 5/18 (2006.01)
B60R 1/00 (2006.01)

(52) U.S. Cl.
CPC ........ *G06K 9/00845* (2013.01); *A61B 5/0077* (2013.01); *A61B 5/165* (2013.01); *A61B 5/18* (2013.01); *B60R 1/00* (2013.01); *G06K 9/0061* (2013.01); *G06K 9/00335* (2013.01); *B60R 2300/8006* (2013.01)

(58) Field of Classification Search
USPC ......................................................... 382/104
See application file for complete search history.

(56) References Cited

U.S. PATENT DOCUMENTS

| 6,426,702 B1* | 7/2002 | Young .................... G08B 21/06 340/309.7 |
| 7,202,792 B2 | 4/2007 | Zhang et al. |
| 7,830,266 B2* | 11/2010 | Nakagoshi ............. G08B 21/06 340/575 |
| 8,519,853 B2* | 8/2013 | Eskandarian ........ A61B 5/6887 180/272 |

(Continued)

FOREIGN PATENT DOCUMENTS

| JP | 2007-072641 A | 3/2007 |
| JP | 4974360 B2 | 7/2012 |

(Continued)

*Primary Examiner* — Ishrat I Sherali
(74) *Attorney, Agent, or Firm* — Mintz Levin Cohn Ferris Glovsky and Popeo, P.C.; Peter F. Corless

(57) ABSTRACT

An apparatus and method for determining drowsiness of a driver are provided. The apparatus includes an imaging device that obtains an image of the driver and a controller that determines (e.g., based on the image of the driver) when the driver is in a fatigue state, when the driver is in an eyelid closure state, and when the driver is in a wake-up state. The controller further determines that the driver is in a drowsiness state when after the fatigue state of the driver continues over a predetermined first time interval, the eyelid closure state and the wake-up state of the driver alternately and repetitively occur within a predetermined second time interval.

6 Claims, 5 Drawing Sheets

(56) References Cited

U.S. PATENT DOCUMENTS

| | | |
|---|---|---|
| 8,537,000 B2 | 9/2013 | Nakagoshi et al. |
| 8,725,311 B1 * | 5/2014 | Breed .................... G08B 21/06 |
| | | 600/300 |
| 9,937,792 B2 * | 4/2018 | Nania .................. B60K 28/066 |
| 9,956,963 B2 * | 5/2018 | Vijaya Kumar ...... B60W 40/08 |
| 2016/0272217 A1 | 9/2016 | Kim et al. |

FOREIGN PATENT DOCUMENTS

| | | |
|---|---|---|
| KR | 10-0295850 B1 | 5/2001 |
| KR | 2005-0108216 A | 11/2005 |
| KR | 10-0630163 B1 | 9/2006 |
| KR | 2011-0052453 A | 5/2011 |
| KR | 10-1386823 B1 | 4/2014 |

* cited by examiner

APPARATUS AND METHOD TO DETERMINE DROWSINESS OF A DRIVER

CROSS-REFERENCE TO RELATED APPLICATION

This application is based on and claims the benefit of priority to Korean Patent Application No. 10-2016-0048915, filed on Apr. 21, 2016 in the Korean Intellectual Property Office, the disclosure of which is incorporated herein in its entirety by reference.

BACKGROUND

Field of Invention

The present disclosure relates to an apparatus and a method for determining drowsiness of a driver, and more particularly, to an apparatus and a method that obtains an image of a driver and determine the drowsiness of the driver based on the image of the driver.

Description of Related Art

Currently, vehicle transportation methods include two-wheel motorcycle, a train, a ship, an airplane, and the like which enable people to freely travel. However, serious injury and property damage of due to a drowsiness driving may occur while a vehicle is being driven. Accordingly, various methods for preventing drowsiness of a driver have been researched.

In particular, when a continuous eyelid closure time of a driver is greater than a first threshold (dTH) an early warning mode is entered and an early warning is maintained until the continuous eyelid closure time of the driver is less than 1 dTH which is less than the first threshold (dTH) to warn a driver of the drowsiness driving. However, when, a warning is output regarding the drowsiness driving based on the threshold of the continuous eyelid closure time, the threshold is set to be high to prevent a misdetection. Accordingly, a non-detection of the drowsiness driving and a warning delay occur.

[NOTE: Please include the above references in Invention Disclosure Statement.] Further, when an eye image of a driver is obtained, a pupil of the eye that is not viewed is determined to be a closed eye. Accordingly, when the closed eye is detected for a constant threshold period of time, the driver is determined to be in a drowsiness state. However, it may be difficult to obtain a pupil image from an infrared image obtained by photographing the driver due to a disturbance of ambient light, reflection of glasses, or the like, and determining drowsiness based on the continuous eyelid closure time may be difficult.

The above information disclosed in this section is merely for enhancement of understanding of the background of the invention and therefore it may contain information that does not form the prior art that is already known in this country to a person of ordinary skill in the art.

SUMMARY

The present disclosure provides an apparatus and a method for determining drowsiness of a driver while a vehicle is being driven within a minimal time interval. Further, an aspect of the present disclosure provides an apparatus and a method for determining drowsiness of a driver capable of reducing misrecognition of a drowsiness driving by a cluster or audio video navigation (AVN) operation.

According to an exemplary embodiment of the present disclosure, an apparatus for determining drowsiness of a driver may include an imaging device configured to obtain an image (e.g., a face or other recognition characteristics) of the driver and a controller configured to determine from the image of the driver when the driver is in a fatigue state, when the driver is in an eyelid closure state, and when the driver is in a wake-up state, and configured to determine that the driver is in a drowsiness state when after the fatigue state of the driver continues over a predetermined first time interval, the eyelid closure state and the wake-up state of the driver alternately and repetitively occur within a predetermined second time interval. The controller may be configured to determine when the driver is in the fatigue state based on at least one of when a percentage of an eye closure of the driver exceeds a preset percentage during a predetermined third time interval or when a face motion of the driver is within a predetermined fourth time interval.

The apparatus may further include a vehicle driving state obtainer configured to obtain a driving state of the vehicle which is driven by the driver, wherein the controller may be configured to determine whether the driver is in the fatigue state based on at least one of when the vehicle deviates from a driving lane and whether or the vehicle is driven in a zigzag direction from the driving state of the vehicle. The controller may be configured to determine whether the driver is in the wake-up state based on at least one of whether an eye blink of the driver occurs within a predetermined fifth time interval or when a face motion of the driver exceeds a preset degree.

According to another exemplary embodiment of the present disclosure, a method for determining drowsiness of a driver may include obtaining by an imaging device an image of the driver, determining, by a controller, from the image of the driver when the driver is in a fatigue state, when the driver is in an eyelid closure state, and when the driver is in a wake-up state and determining, by the controller, that the driver is in a drowsiness state when, after the fatigue state of the driver continues over a predetermined first time interval, the eyelid closure state and the wake-up state of the driver occur alternately and repetitively within a predetermined second time interval. The determination of when the driver is in the fatigue state may be determined based on at least one of when an eyelid closure time of the driver exceeds a predetermined third time interval or when a face motion of the driver is within a predetermined fourth time interval.

The method may further include detecting a driving state of a vehicle which is driven by the driver, wherein when the driver is in the fatigue state may be determined based on at least one of the vehicle's deviates from a driving lane a lane or when the vehicle is driven in a zigzag direction from the driving state of the vehicle. The determination of when a driver is in the wake-up state may be determined based on at least one of when an eye blink of the driver occurs within a predetermined fifth time interval or when a face motion of the driver exceeds a preset degree.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
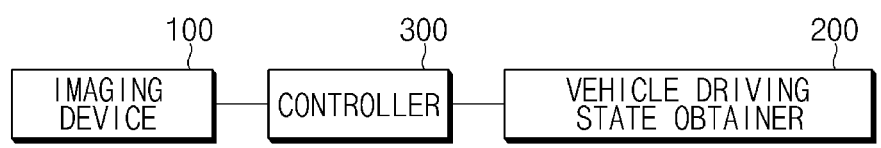
FIG. 1 is an exemplary block diagram of an apparatus to determine drowsiness of a driver according to an exemplary embodiment of the present disclosure.

Hereinafter, some exemplary embodiments of the present disclosure will be described in detail with reference to the illustrative drawings. It is to be noted that in giving reference numerals to components of each of the accompanying drawings, the same components will be denoted by the same reference numerals even though they are shown in different drawings. Further, in describing exemplary embodiments of the present disclosure, well-known constructions or functions will not be described in detail in the case in which they may unnecessarily obscure the understanding of the exemplary embodiments of the present disclosure.

In describing the components of exemplary embodiments of the present disclosure, terms such as first, second, A, B, (a), (b), etc. can be used. These terms are used only to differentiate the components from other components. Therefore, the nature, order, sequence, etc. of the corresponding components are not limited by these terms. In addition, unless defined otherwise, it is to be understood that all the terms used in the specification including technical and scientific terms have the same meaning as those that are understood by those skilled in the art to which the present disclosure pertains. It should be understood that the terms defined by the dictionary are identical with the meanings within the context of the related art, and they should not be ideally or excessively formally construed unless clearly defined otherwise in the present application.

Furthermore, control logic of the present invention may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

It is understood that the term "vehicle" or "vehicular" or other similar term as used herein is inclusive of motor vehicle in general such as passenger automobiles including sports utility vehicles (SUV), buses, trucks, various commercial vehicles, watercraft including a variety of boats, ships, aircraft, and the like and includes hybrid vehicles, electric vehicles, combustion, plug-in hybrid electric vehicles, hydrogen-powered vehicles and other alternative fuel vehicles (e.g. fuels derived from resources other than petroleum).

Figure 2:
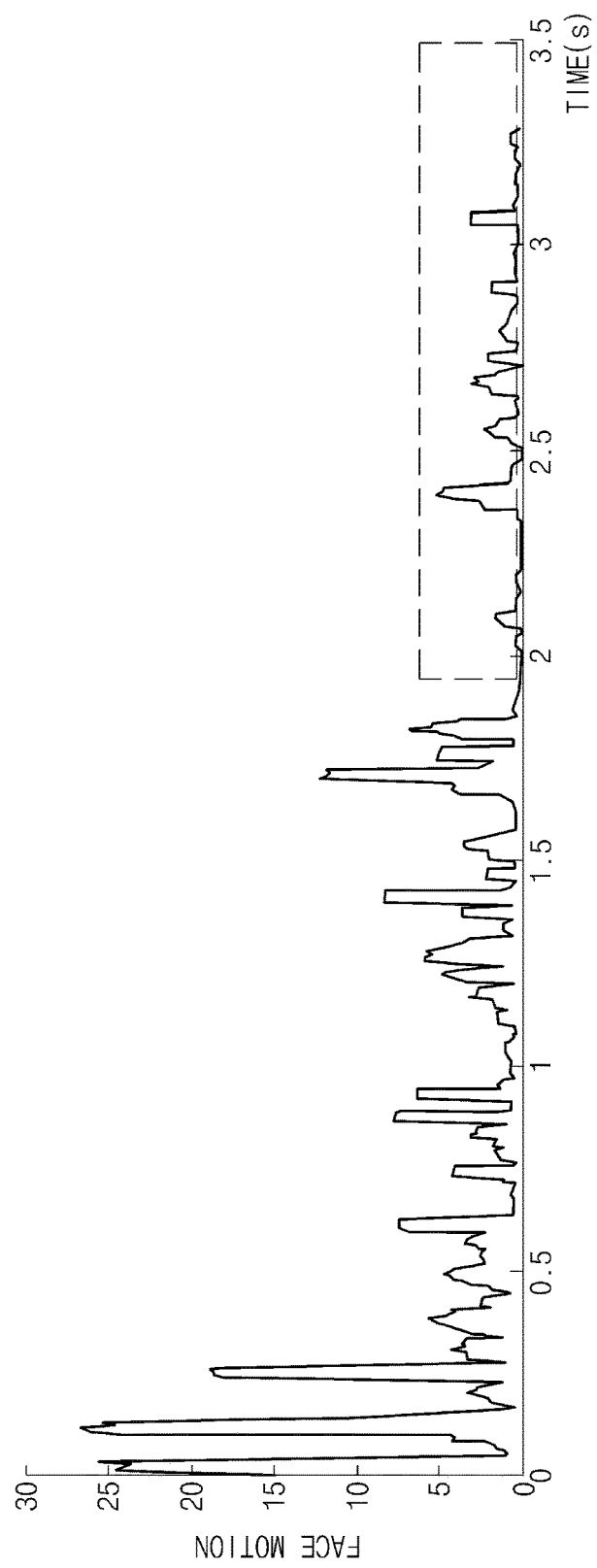
FIG. 2 is an exemplary graph illustrating a face motion of a driver to determine when the driver is in a fatigue state according to an exemplary embodiment of the present disclosure.
Figure 3:
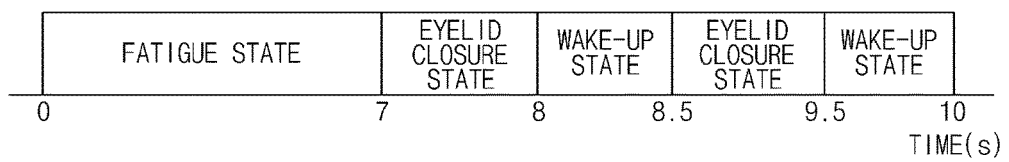
FIG. 3 is an exemplary diagram illustrating a pattern for determining drowsiness of a driver according to an exemplary embodiment of the present disclosure.

FIG. 1 is an exemplary block diagram of an apparatus for determining drowsiness of a driver according to an exemplary embodiment of the present disclosure. FIG. 2 is an exemplary graph illustrating a face motion of a driver to determine when the driver is in a fatigue state according to an exemplary embodiment of the present disclosure. FIG. 3 is an exemplary diagram illustrating a pattern for determining drowsiness of a driver according to an exemplary embodiment of the present disclosure.

First, referring to FIG. 1, an apparatus for determining drowsiness of a driver may include an imaging device 100 (e.g., a camera, a video camera or the like), a vehicle driving state obtainer 200, and a controller 300. The controller may be configured to operate the imaging device 100 and the driving state obtainer 200. However, the components illustrated in FIG. 1 are not essential components. Therefore, the apparatus for determining drowsiness of a driver having components more or less than the components illustrated in FIG. 1 may also be implemented. The imaging device 100 may be configured to obtain an image (e.g., a facial recognition) of the driver. The imaging device 100 may be a camera configured to photograph a face (or a portion thereof) of the driver within a vehicle and may also be an image receiver configured to obtain an image from the camera. Further, the vehicle driving state obtainer 200 may be configured to obtain a driving state of a vehicle which is driven by the driver. The vehicle driving state obtainer 200 may obtain information including but not limited to a driving direction of the vehicle, driving velocity of the vehicle, a distance between the vehicle and a vehicle in front, whether the vehicle deviates from the driving lane (e.g., the vehicle violates a lane of a road), and the like.

Further, the controller 300 may be configured to determine a drowsiness state of the driver, may determine when the driver is in a fatigue state, when the driver is in an eyelid closure state, and when the driver is in a wake-up state based on the image of the driver obtained by the imaging device 100 and the driving state of the vehicle obtained by the vehicle driving state obtainer 200. Accordingly, the controller may be configured to determine when the driver is in a drowsiness state based on when the driver is in the fatigue state, when the driver is in the eyelid closure state, and when the driver is in the wake-up state.

The controller 300 may consider when a percentage of an eye closure (PERCLOS) of the driver during a predetermined time exceeds a constant percentage, when the face motion of the driver is within a predetermined range over a predetermined time, when the vehicle is driven within the driving lane, when the vehicle is driven in a zigzag pattern, or the like, to determine when the driver is in the fatigue state. For example, when the constant percentage is set to about 10%, and a time in which an eye of the driver is closed (e.g., is about 6 seconds or greater during 60 seconds), the controller 300 may be configured to determine that the driver is in the fatigue state.

Additionally, referring to FIG. 2, a section in which the face motion of the driver is maintained in the range of about 1 second or greater to about 5 seconds does not exist up to about 2 seconds. However, the face motion of the driver may be maintained in the range of about 1 second or greater to about 5 seconds in a section from about 2 seconds to about 3 seconds. In particular, when the face motion of the driver is minimal with respect to a constant time interval, the controller 300 may be configured to determine that the driver is in the fatigue state. Further, when the vehicle is driven continuously changing lanes or deviating from the driving lane (e.g., without keeping within the driving lane) or when the vehicle is driven in the zigzag pattern from the driving state of the vehicle, the controller 300 may be configured to determine that the driver is in the fatigue state. A method of determining, by the controller 300, when the driver is in the fatigue state may be a combination of illustrated methods, and are not limited to the illustrated methods.

The controller 300 may be configured to determine when the driver is in the eyelid closure state by recognizing when an eyelid of the driver is closed based on the image of the driver. Further, the controller 300 may be configured to determine when an eye blink of the driver is a normal eye blink or when the face motion of the driver exceeds a constant degree to determine when the driver is in the wake-up state. For example, the normal eye blink may include an eye blink when the driver is not in the drowsiness state, and may include the eye blink performed within a constant time interval. In particular, when the driver blinks eyes in the drowsiness state, a time interval when the eyes of the driver are closed in one eye blink is a greater duration than the normal eye blink.

The controller 300 may be configured to determine when the driver is in the wake-up state based on the occurrence of the normal eye blink. Additionally, the face motion of the driver may include a change in a direction to which the face of the driver is directed or a change in a position of the face. When the face motion of the driver exceeds a constant degree, the controller 300 may be configured to determine when the driver is in the wake-up state. A method of determining, by the controller 300, when the driver is in the wake-up state may be a combination of illustrated methods, and are not limited to the illustrated methods.

In other words after the fatigue state of the driver continues for a first time interval or more than a first time interval, the eyelid closure state and the wake-up state of the driver during a third time range may occur alternately and repetitively within a second time, the controller 300 may be configured to determine that the driver is in the drowsiness state based on when the driver is in the fatigue state, when the driver is in the eyelid closure state, and when the driver is in the wake-up state which are determined as described above.

For example, when the first time is set to about 5 seconds, the second time is set to about 4 seconds, and the third time range may be set to about 0.5 seconds or greater to about 1.5 seconds or less will be described as an example with reference to the pattern illustrated in FIG. 3 from which the controller 300 may be configured to determine the drowsiness state of the driver. A time interval in which the fatigue state continues may be about 7 seconds, and continues for about 5 seconds, which is the first time interval. Thereafter, the eyelid closure state of the driver may occur during about 1 second, which is within the third time interval. Additionally, after the eyelid closure state occurs, the wake-up state occurs, and after the eyelid closure state again occurs for about 1 second, the wake-up state occurs. In other words, the eyelid closure state and the wake-up state may occur alternately and repetitively. In particular, the eyelid closure state and the wake-up state may occur alternately and repetitively between about 7 seconds and about 10 seconds and occur within about 4 seconds, which is the second time interval. Accordingly, when the fatigue state occurs, the eyelid closure state and the wake-up state of the driver occur, and the controller 300 may be configured to determine that the driver is in the drowsiness state.

Figure 4:
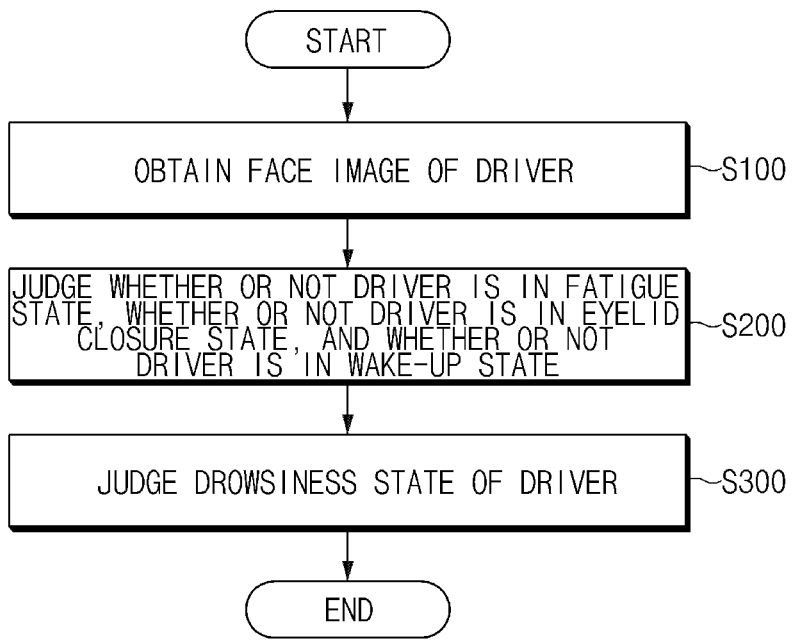
FIG. 4 is an exemplary flow chart illustrating a method for determining drowsiness of a driver according to an exemplary embodiment of the present disclosure.

Hereinafter, a method for judging drowsiness of a driver will be described in detail with reference to FIG. 4 based on the configurations described above. FIG. 4 is an exemplary flow chart illustrating a method for determining drowsiness of a driver according to an exemplary embodiment of the present disclosure. Referring to FIG. 4, a method for determining drowsiness of a driver according to an exemplary embodiment of the present disclosure may include obtaining an image of a driver S100, determining from the image of the driver when the driver is in a fatigue state, when the driver is in an eyelid closure state, and when the driver is in a wake-up state S200 and determining that the driver is in a drowsiness state, when, after the fatigue state of the driver continues over a predetermined first time interval, the eyelid closure state and the wake-up state of the driver alternately and repetitively occur within a predetermined second time interval S300.

The imaging device 100 may be configured to obtain the image (e.g. face image) of the driver S100. The imaging device 100 may be configured to obtain the image of the driver by photographing a face of the driver (e.g., or a portion thereof) and may also obtain an image from a camera as an image receiver. Further, the vehicle driving state obtainer 200 according to an exemplary embodiment of the present disclosure may be configured to obtain a driving state of a vehicle which is driven by the driver S200. The vehicle driving state obtainer 200 may obtain information that includes a driving direction of the vehicle, driving velocity of the vehicle, a distance between the vehicle and a vehicle in front, whether or not the vehicle violates a lane of a road, and the like. The various driving state information may be detected using various sensors mounted within the vehicles.

The controller 300 may be configured to determine from the image of the driver when the driver is in the fatigue state S200, when the driver is in the eyelid closure state, and when the driver is in the wake-up state. The controller 300 may use information related to when a percentage of an eye closure (PERCLOS) of the driver during a predetermine time exceeds a constant percentage, when a face motion of the driver is within a predetermined range over a predetermine time, when the vehicle keeps the lane, whether the vehicle is driven in a zigzag pattern, or the like, to determine when the driver is in the fatigue state. Additionally, the controller 300 may be configured to determine when the driver is in the eyelid closure state by recognizing when an eyelid of the driver is closed based on the image of the driver. In particular, the controller 300 may consider when an eye blink of the driver is a normal eye blink or when the face motion of the driver exceeds a constant degree to determine when the driver is in the wake-up state.

After the fatigue state of the driver continues for a first time interval or greater, the eyelid closure state and the wake-up state of the driver during a third time range occur alternately and repetitively within a second time S300. The controller 300 may be configured to determine that the driver is in the drowsiness state based on the driver's fatigue state, when the driver is in the eyelid closure state, and when the driver is in the wake-up state which are determined as described above. The controller 300 may further be configured to determine the drowsiness state based on the pattern illustrated in FIG. 3, and since a detailed method thereof has been described above with reference to FIG. 3, it will be omitted.

Figure 5:
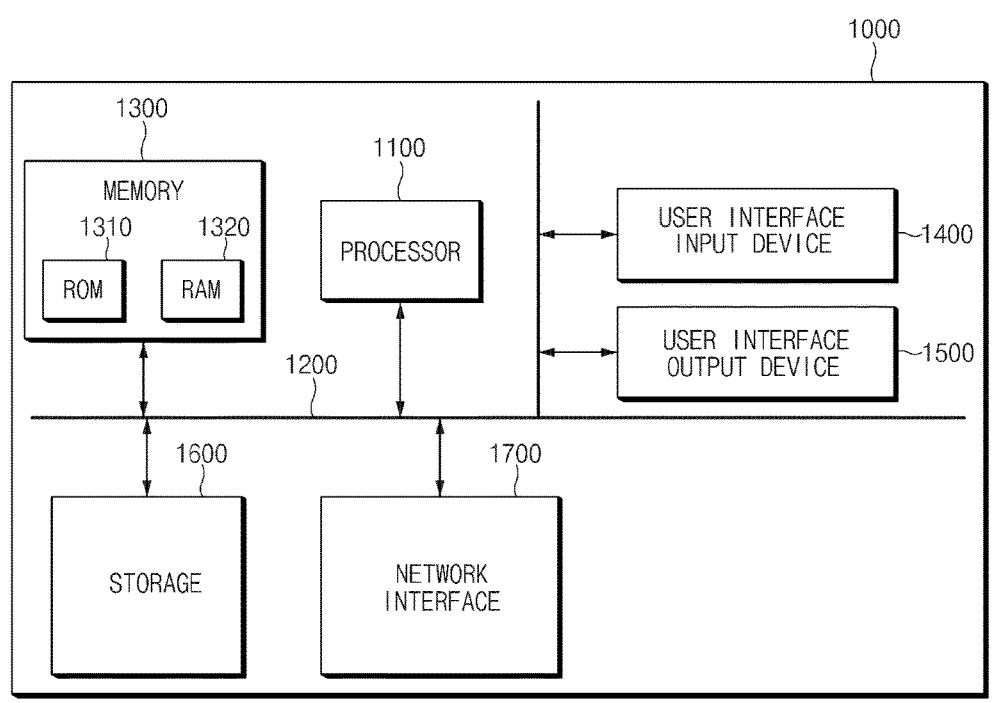
FIG. 5 is an exemplary block diagram illustrating a computing system executing the method for determining drowsiness of a driver according to an exemplary embodiment of the present disclosure.

FIG. 5 is an exemplary block diagram illustrating a computing system executing the method for determining drowsiness of a driver according to an exemplary embodiment of the present disclosure. Referring to FIG. 5, a computing system 1000 may include at least one processor 1100, a memory 1300, a user interface input device 1400, a user interface output device 1500, a storage 1600, and a network interface 1700 connected to each other via a bus 1200. The processor 1100 may be a central processing unit (CPU) or a semiconductor device configured to execute processes for instructions which are stored in the memory 1300 and/or the storage 1600. The memory 1300 and the storage 1600 may include various types of volatile or non-volatile storing media. For example, the memory 1300 may include a read only memory (ROM) and a random access memory (RAM).

Accordingly, steps in the method or algorithm which is described in context with the exemplary embodiments disclosed in the present specification may be directly implemented in hardware, a software module, or a combination thereof which is executed by the processor 1100. The software module may be resided on a storing medium (i.e., the memory 1300 and/or the storage 1600) such as a random access memory (RAM) memory, a flash memory, a read only memory (ROM) memory, an erasable programmable read only memory (EPROM) memory, an electrically erasable programmable read only memory (EEPROM) memory, a register, a hard disk, a removable disk, or a compact disc-read only memory (CD-ROM). An illustrative storing medium may be coupled to the processor 1100, and the processor 1100 may read information from the storing medium and write the information into the storing medium. Alternatively, the storing medium may also be integral with the processor 1100. The processor and the storing medium may also be resided within an application specific integrated circuit (ASIC). The ASIC may also be resided within a user terminal. Alternatively, the processor and the storing medium may also be resided within the user terminal as an individual component.

In the apparatus and the method to determine drowsiness of a driver as described above, the configuration and the method of the above-mentioned exemplary embodiments are not restrictively applied. In other words, all or some of the respective exemplary embodiments may be selectively combined with each other so that they may be variously modified. As described above, according to the exemplary embodiments of the present disclosure, the drowsiness of the driver which may occur during operation of the vehicle may be determined within a reduced time duration as compared with current drowsiness determination methods. Further, the misrecognition of the drowsiness that may occur when based on the cluster or audio video navigation (AVN) operation may be reduced. Additionally, effects obtained by the present disclosure are not limited to the above-mentioned effects. In particular, other effects that are not mentioned may be obviously understood by those skilled in the art to which the present disclosure pertains from the following description.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An apparatus for determining drowsiness of a driver of a vehicle, comprising:
   an imaging device configured to obtain an image of the driver; and
   a controller configured to determine a fatigue state of the driver, an eyelid closure state of the driver, and a wake-up state of the driver from the image of the driver,
   wherein the controller is configured to determine that the driver is in a drowsiness state when, after the fatigue state of the driver continues over a predetermined first time interval, and the eyelid closure state and the wake-up state of the driver occur alternately and repetitively within a predetermined second time interval, and
   wherein the controller is configured to determine the fatigue state of the driver based on at least one of when the vehicle deviates from a driving lane or when the vehicle is driven in a zigzag direction from a driving state of the vehicle.

2. The apparatus according to claim 1, wherein the controller is configured to determine when the driver is in the fatigue state based on at least one of when a percentage of an eye closure of the driver exceeds a preset percentage during a predetermined third time interval and when a face motion of the driver is within a predetermined fourth time interval.

3. The apparatus according to claim 1, wherein the controller is configured to determine when the driver is in the wake-up state based on at least one of an eye blink of the driver that occurs within a predetermined fifth time interval and when a face motion of the driver exceeds a preset degree.

4. A method for determining drowsiness of a driver of a vehicle, comprising:
   obtaining, by an imaging device, an image of the driver;
   determining, by a controller, a fatigue state of the driver, an eyelid closure state of the driver and a wake-up state of the driver from the image; and
   determining, by the controller, that the driver is in a drowsiness state when after the fatigue state of the driver continues over a predetermined first time interval, the eyelid closure state and the wake-up state of the driver occur alternately and repetitively within a predetermined second time interval,
   wherein the determining of the fatigue state of the driver comprises determining, by the controller, the fatigue state of the driver based on at least one of when the vehicle deviates from a driving lane or when the vehicle is driven in a zigzag direction from a driving state of the vehicle.

5. The method according to claim 4, wherein when the driver is in the fatigue state is determined based on at least one of when an eyelid closure time of the driver exceeds a predetermined third time interval and when a face motion of the driver is within a predetermined fourth time interval.

6. The method according to claim 4, wherein when the driver is in the wake-up state is determined based on at least one of when an eye blink of the driver occurs within a predetermined fifth time interval or when a face motion of the driver exceeds a preset degree.

\* \* \* \* \*